United States Patent
Llop

(10) Patent No.: US 10,517,694 B2
(45) Date of Patent: *Dec. 31, 2019

(54) IMPLANT-BASED ATTACHMENT SYSTEM FOR DENTAL IMPLANT SURGICAL GUIDE AND METHOD

(71) Applicant: National Dentex, LLC, Palm Beach Gardens, FL (US)

(72) Inventor: Daniel R. Llop, Reno, NV (US)

(73) Assignee: National Dentex, LLC, Palm Beach Gardens, FL (US)

( * ) Notice: Subject to any disclaimer, the term of this patent is extended or adjusted under 35 U.S.C. 154(b) by 220 days.

This patent is subject to a terminal disclaimer.

(21) Appl. No.: 15/634,773

(22) Filed: Jun. 27, 2017

(65) Prior Publication Data
US 2017/0290638 A1 Oct. 12, 2017

Related U.S. Application Data

(63) Continuation of application No. 14/487,075, filed on Sep. 15, 2014, now Pat. No. 9,693,834.

(60) Provisional application No. 61/877,648, filed on Sep. 13, 2013.

(51) Int. Cl.
*A61C 8/00* (2006.01)
*A61C 1/08* (2006.01)

(52) U.S. Cl.
CPC ............. *A61C 1/084* (2013.01); *A61C 8/005* (2013.01); *A61C 8/0048* (2013.01); *A61C 8/0068* (2013.01); *A61C 8/0069* (2013.01); *A61C 8/0089* (2013.01)

(58) Field of Classification Search
CPC ....... A61C 1/084; A61C 8/0048; A61C 8/005; A61C 8/0068; A61C 8/0069; A61C 8/0089
See application file for complete search history.

(56) References Cited

U.S. PATENT DOCUMENTS

| | | |
|---|---|---|
| 9,173,723 B2 | 11/2015 | Harrison |
| 9,226,801 B2 | 1/2016 | Groscurth et al. |
| 9,408,678 B2 | 8/2016 | Harrison |
| 9,498,307 B2 | 11/2016 | Harrison |

(Continued)

OTHER PUBLICATIONS

U.S. Appl. No. 61/877,648, filed Sep. 13, 2013.

*Primary Examiner* — Ralph A Lewis
(74) *Attorney, Agent, or Firm* — Frost Brown Todd LLC

(57) ABSTRACT

The disclosure relates to methods for attaching a dental implant surgical guide and a dental implant to a dental surgical site including: assembling an implant combination, positioning the dental implant surgical guide including a double open-ended guide cylinder at the dental surgical site; rotating the implant combination through the double open-ended guide channel; and attaching a cap comprising a hollow cylinder to the double open-ended guide channel so the rim of the implant mount body is sandwiched between the dental surgical guide and the cap. The disclosure further relates to a dental prosthesis apparatus including: an abutment; a dental implant; a dental implant surgical guide including a first and a second double open-ended guide cylinder connected by a support bar; an implant mount including a rim; and a cap operable to engage the dental implant surgical guide and sandwich the rim between the cap and the dental implant surgical guide.

20 Claims, 9 Drawing Sheets

(56) References Cited

U.S. PATENT DOCUMENTS

| | | |
|---|---|---|
| 9,504,533 B2 | 11/2016 | Groscurth et al. |
| 9,554,879 B2 | 1/2017 | Harrison |
| 9,693,834 B2 * | 7/2017 | Llop .................... A61C 8/0048 |
| 2009/0130630 A1 | 5/2009 | Suttin et al. |
| 2009/0298008 A1 | 12/2009 | Groscurth et al. |
| 2010/0124731 A1 | 5/2010 | Groscurth et al. |
| 2011/0045431 A1 | 2/2011 | Groscurth et al. |
| 2011/0045432 A1 | 2/2011 | Groscurth et al. |
| 2016/0106517 A1 | 4/2016 | Groscurth et al. |
| 2016/0324599 A1 | 11/2016 | Harrison |
| 2017/0071697 A1 | 3/2017 | Groscurth et al. |
| 2017/0112592 A1 | 4/2017 | Groscurth et al. |

* cited by examiner

IMPLANT-BASED ATTACHMENT SYSTEM FOR DENTAL IMPLANT SURGICAL GUIDE AND METHOD

CROSS REFERENCE TO RELATED APPLICATIONS

This application is a Continuation Application of Applicant's patent application Ser. 14/487,075 filed in the U.S. Patent & Trademark Office on Sep. 15, 2014, which claims benefits and priority to U.S. Provisional Application 61/877,648, filed on Sep. 13, 2013.

BACKGROUND

The present invention may relate to the implant attachment systems for attaching dental implant surgical guides to dental implants. More specifically, the present invention may relate to those implant attachment means that are used on dental implant surgical guides that may be subsequently incorporated into dental prostheses.

Dental implant surgical guides may be used for the placement of implant drills, implant reamers, dental implants, and other dental implements at a dental implant site in a mouth of a patient to help ensure that such placed dental implements achieve the proper and desired telemetry and location. Similarly, dental implant surgical guides can be used in practice on a model of a patient's mouth to test the placement and positioning of dental implements. Normally after the implants (e.g., post-type implants) have been placed in the mouth through the use of the dental implant surgical guide, the dental implant surgical guide could be removed from the mouth and generally be discarded. In some dental implant/prosthesis surgeries, a connecting bar may be further attached to the dental implants to substantially form a bar/implant configuration for the dental prosthesis attachment. After suitable testing and fitting, a prosthesis may then be attached to the dental implants and/or connecting bar/implant configuration to secure the dental prosthesis in the patient's mouth.

It has been found that the dental implant surgical guide could be used to replace the connecting bar to save on costs and labor in the implant process. The dental implant surgical guide can be further incorporated into the dental prosthesis by attaching the dental implant surgical guide within an open channel in the bottom of the dental prosthesis or by generally being enclosed within the dental prosthesis interior formed by two halves of a prosthesis. Rather than discarding the dental implant surgical guide, the dental implant surgical guide can be added to the dental prosthesis structure to generally increase the structural integrity and load-carrying capacity of the dental prosthesis.

One possible issue with the incorporation of the dental implant surgical guide into the dental prosthesis could be the attachment of the dental implant surgical guides to the placed dental implants. Generally to control the telemetry and position of the implants, dental implant surgical guides may have guide cylinders forming double open-ended guide channels through which the dental implants may pass to be located to the respective dental surgical site (or dental surgical site model). As such, dental implant surgical guides when located over the dental implants may have an open area, the guide channel, that is directly located over the placed implant thereby generally eliminating any material (e.g., metal) that may rest upon and be subsequently used to attach the dental implant surgical guide to the implant.

One possible solution to this issue could the present invention's attachment system of an abutment, an implant mounting and a cap. The abutment and implant mounting being combined with an otherwise unsecured implant outside of the dental implant surgical guide (e.g., outside of the patient's mouth) to form an implant combination wherein the implant, implant abutment, and most of the implant mount are able to pass though the guide channel. The implant mount at its otherwise unattached end could have a rim with a greater diameter/circumference than that of the guide channel so that the rim cannot pass through the guide channel. In this implant combination, the implant mount may be attached to one abutment end of the abutment, the abutment may be attached by its other abutment end to the implant to create a generally an overall columnar form. The assembled implant combination can then be inserted into the respective guide channel of the surgical guide. The implant mount can be engaged by a tool (e.g., wrench) so the entire combination can be moved within the guide channel to substantially allow threads of the implant to substantially engage the prepared implant shaft at the dental implant site. As the implant combination is generally secured to the dental surgical site (or model thereof), the rim may be drawn into contact with the top of guide cylinder. In this manner, the rim overall anchors the dental implant surgical guide to the implant in a manner that resists those outward forces that may pull the dental implant surgical guide way from the dental implant.

The cap could be subsequently attached to the top of the guide cylinder to sandwich the rim between the guide cylinder and cap to substantially resist those forces which may direct the dental implant surgical guide towards the implant. This cap attachment action may also move the dental implant surgical guide up tight against the rim in a manner to further bring the dental implant surgical guide into a more complete alignment with the placed implants.

SUMMARY OF ONE EMBODIMENT OF THE INVENTION

Advantages of One or More Embodiments of the Present Invention

The various embodiments of the present invention may, but do not necessarily, achieve one or more of the following advantages:

the ability to attach a dental implant surgical guide to one or more dental implants to resist pressure upon the dental implant surgical guide that moves the dental implant surgical guide either towards or away from the one or more of the dental implants;

provide a system that attaches the dental implant surgical guide to the one or more implants to allow the dental implant surgical guide to support a dental prosthesis;

the ability to secure the dental prosthesis to the dental implant surgical guide as a way of attaching the dental prosthesis to the one or more dental implants;

provide a securing system that attaches the dental implant surgical guide to one or more implants in a manner that allows a dental prosthesis to connect to the dental implant guide as way of anchoring the dental prosthesis to a patient's mouth;

the ability to reuse a dental implant surgical guide to anchor an dental prosthesis to a patients mouth or a model of a patient's mouth or alike;

provide outside a patient's mouth, an implant combination, an implant mount connected to an abutment secured to an implant, the implant combination placed in the dental implant surgical guide and being rotated to attach the surgical guide to the implant;

provide a fastener-to-fastener connection to secure the dental implant surgical guide to the one or more dental implants;

the ability to place a cap over the implant mount to secure a rim of the implant mount in between the cap and the dental implant surgical guide in a manner that locks in a final positioning of the dental implant surgical guide to the one or more dental implants;

provide the cap that attaches to the dental implant surgical guide to bring the dental implant surgical guide into final and proper positioning relative to the one or more dental implants; and the ability to attach the dental implant surgical guide to the one or more implants to allow the dental implant surgical guide to be encompassed by a dental prosthesis.

These and other advantages may be realized by reference to the remaining portions of the specification, claims, and abstract.

BRIEF DESCRIPTION OF ONE EMBODIMENT OF THE PRESENT INVENTION

One possible embodiment of the invention could include a system for attaching a dental implant surgical guide to one or more dental implants comprising: an abutment capable of connecting to at least one of the one or more dental implants and to an implant mount; the implant mount having an implant mount body with a first mount end that connects accepts a portion of the abutment and a second mount end that has a rim that cannot pass through the dental implant surgical guide; and a cap that is comprised of a hollow cylinder with an enclosed cap end and an open cap end, the cap being capable of engaging a dental implant surgical guide so to sandwich the rim between the cap and the dental implant surgical guide.

Another possible embodiment of the invention could include a method of attaching a dental implant surgical guide to one or more dental implants comprising of the following steps, providing a dental implant that has a first implant end capable of attaching to a dental implant site and a second implant end capable of attaching to an abutment; providing a dental implant surgical guide comprising a guide body that defines a set of spaced-apart guide cylinders, each guide cylinder being penetrated by respective double open-ended guide channel; providing the abutment comprising an abutment body denoting a first abutment end that can attach to the implant and a second abutment end that can attach to an implant mount; providing the implant mount with a mount body forming a first mount end that can accept a portion of the abutment and a second mount end that has a rim that cannot pass through the guide channel; providing a cap that can attach to the dental surgical guide; forming an implant combination by attaching the abutment to the implant and by attaching the implant mount to the abutment; inserting the implant combination through a guide channel to allow the implant to come into contact with a dental surgical site; rotating the implant combination through the dental surgical guide to secure the implant to either the dental surgical site or the model of the dental surgical site; and attaching the cap to the dental surgical guide to sandwich the rim between dental surgical guide and the cap.

Still yet another embodiment of the invention could be a combination of a dental implant surgical guide connected to one or more dental implants comprising the dental implant surgical guide having a body forming a set of spaced-apart guide cylinders, each guide cylinder denoting a double open-ended guide channel through which the dental implant is passed through to attach to a dental surgical site; an implant combination that is comprised of one dental implant of the one or more implants, the one dental implant attaches to an abutment, the abutment being attaches to an implant mount, the implant mount having one mount end that forms a rim that can rest against the respective guide cylinder; a cap that fits over the rim to attach to the respective guide cylinder; wherein the implant combination is inserted into and rotated within the respective guide cylinder's guide channel to anchor the dental implant of the implant combination to dental implant surgical guide.

The above description sets forth, rather broadly, a summary of one embodiment of the present invention so that the detailed description that follows may be better understood and contributions of the present invention to the art may be better appreciated. Some of the embodiments of the present invention may not include all of the features or characteristics listed in the above summary. There are, of course, additional features of the invention that will be described below and will form the subject matter of claims. In this respect, before explaining at least one preferred embodiment of the invention in detail, it is to be understood that the invention is not limited in its application to the details of the construction and to the arrangement of the components set forth in the following description or as illustrated in the drawings. The invention is capable of other embodiments and of being practiced and carried out in various ways. Also, it is to be understood that the phraseology and terminology employed herein are for the purpose of description and should not be regarded as limiting.

DESCRIPTION OF CERTAIN EMBODIMENTS OF THE PRESENT INVENTION

In the following detailed description of the preferred embodiments, reference is made to the accompanying drawings, which form a part of this application. The drawings show, by way of illustration, specific embodiments in which the invention may be practiced. It is to be understood that other embodiments may be utilized and structural changes may be made without departing from the scope of the present invention.

The present invention 10 could comprise an attachment system 20 and method or process 200 for operating same to attach a dental implant surgical guide to one or more dental implants located at a dental surgical site in a patient's mouth. The employment of the attachment system could allow the dental implant surgical guide to anchor a dental prosthesis to a patent's mouth.

Figure 1:
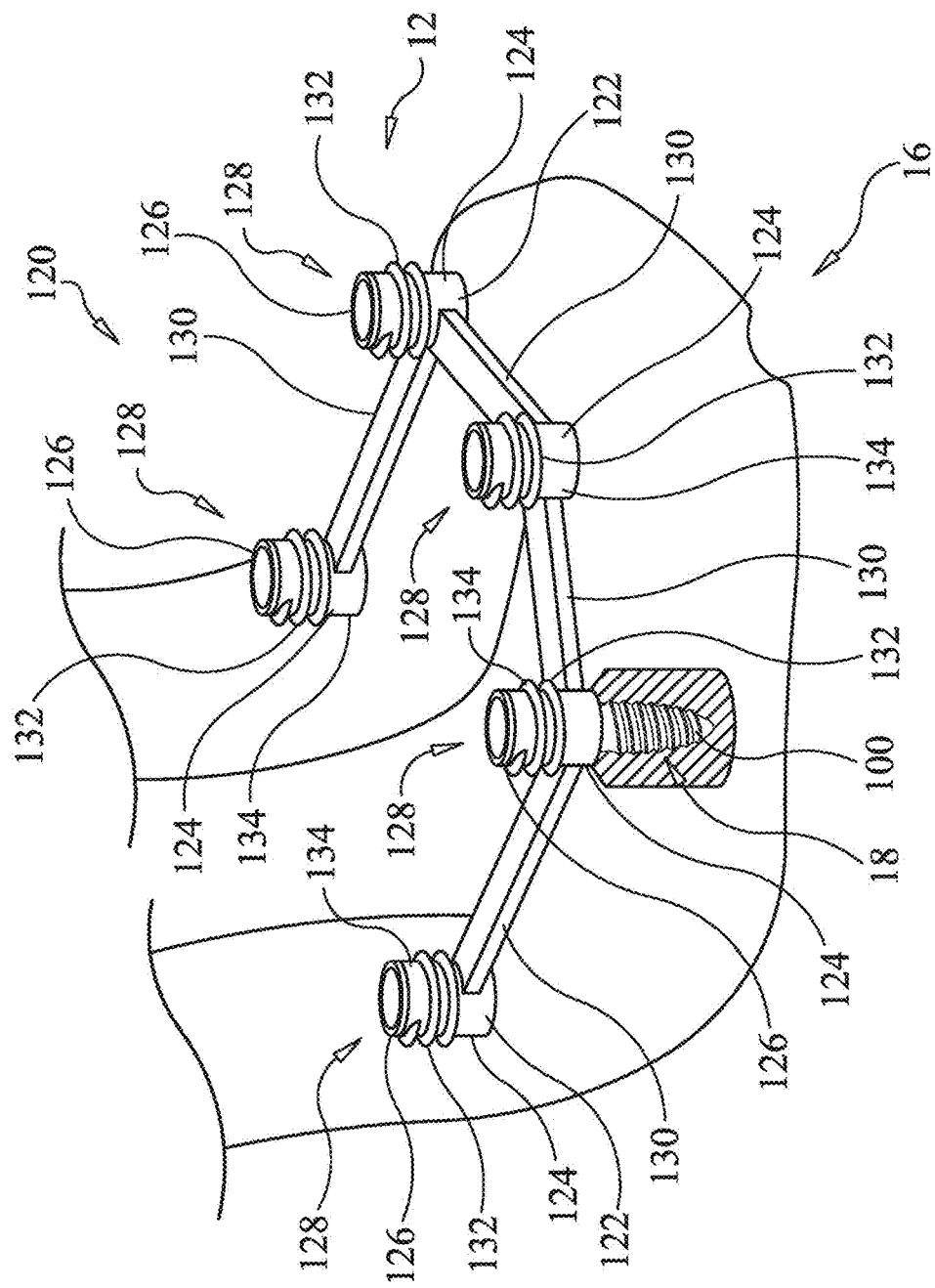
FIG. 1 is substantially perspective cutaway view of one version of a dental implant surgical guide as used in the present invention as placed in a lower jaw of a patient's mouth.

As substantially shown in FIG. 1, a dental implant surgical guide 120 may be used to place one or more dental implants 100 at dental surgical site 12 in an implant shaft 18 at patient's mouth 16 or place dental implant analogues (not shown) in a model of the dental surgical site (not shown). A dental implant surgical guide 120 could comprise a guide body 122 that forms a set of spaced-apart guide cylinders 124. In one possible version, the guide cylinders 124 could be held apart by support bars 130 each having a trapezoidal cross-shape, the trapezoid's narrow flat being on the top of the support bar 130. The trapezoid cross-shape could be conductive to mount the prosthesis 140 (as substantially shown in FIGS. 3 and 11) to the dental implant surgical guide 120. Each guide cylinder 124 further forming double open-ended guide channel 128 that can continuously connect the dental implant surgical guide's top and bottom. The guide channel 128 can be confirmed to specifically receive various dental implements (e.g., implant drills, implant reamers, dental implants 100 and the like) to allow the securing of the dental implants 100 to a dental surgical site 12 of a patient's mouth 16 or to place dental implant analogues to dental surgical site models (not shown.) For use with the invention 10, the external side 134 of the guide cylinder 124 could feature a suitable locking interface 132 (e.g., be threaded) to allow attachment of a cap 72 (as substantially shown in FIGS. 4, 7, 10 and 11) to the guide cylinder top 126.

Figure 2:
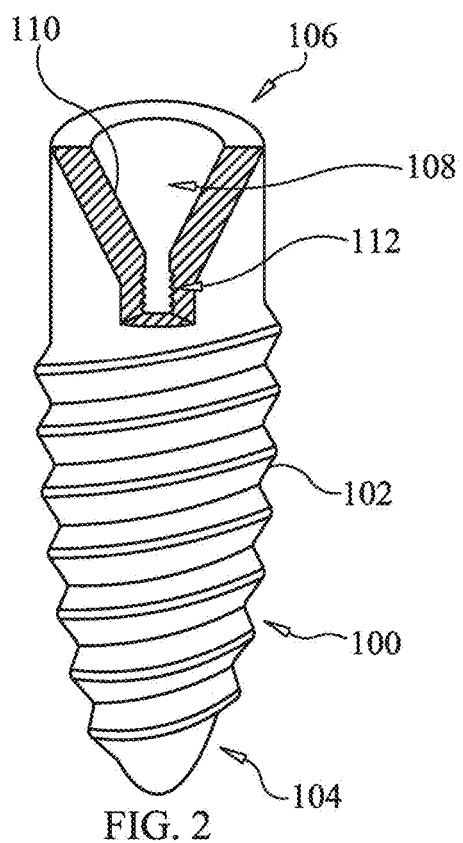
FIG. 2 is substantially a perspective cutaway review of one version of the implant as used with the present invention.

As substantially shown in FIG. 2, the dental implant 100 could be a standard post implant that may have a cylindrical implant body 102 with first tapered and threaded end 104 that that may be used to anchor the dental implant 100 to a bone at the dental surgical site 12. In some versions of the dental implant 100, the second implant end 106 have an open-ended implant recess 108 to accept the first abutment end 34 in a manner to attach the abutment 30 to the dental implant 100 by a variety of attachment devices (e.g., fastener, adhesive, and other securing means known in the art). (As substantially shown in FIG. 4). In one possible embodiment, the implant recess 108 may have a tapered side 110 (e.g., may be cone shaped) to substantially implement a Morse's taper or a taper interference fit as generally known in the art to attach a first abutment end 34 to the implant recess 108. Further, the tip of the implant recess 108 (e.g., tip of the cone) could generally define an implant aperture 112 suitably configured (e.g., threaded) to receive and attached to at least a portion of a first fastener 40. The first fastener 40 in this manner could be initially be used to secure the abutment 30 and dental implant 100 together (as substantially shown in FIG. 4). It should be noted that an analogue implant (not shown) with generally the same attributes as the described dental implant 100 could be substituted for the implant 100 to allow the invention 10 to apply a dental implant surgical guide to a dental surgical site model for testing, fitting and modification of the dental implant surgical guide, the prosthesis, the invention 10 and the like as needed (not shown).

Figure 3:
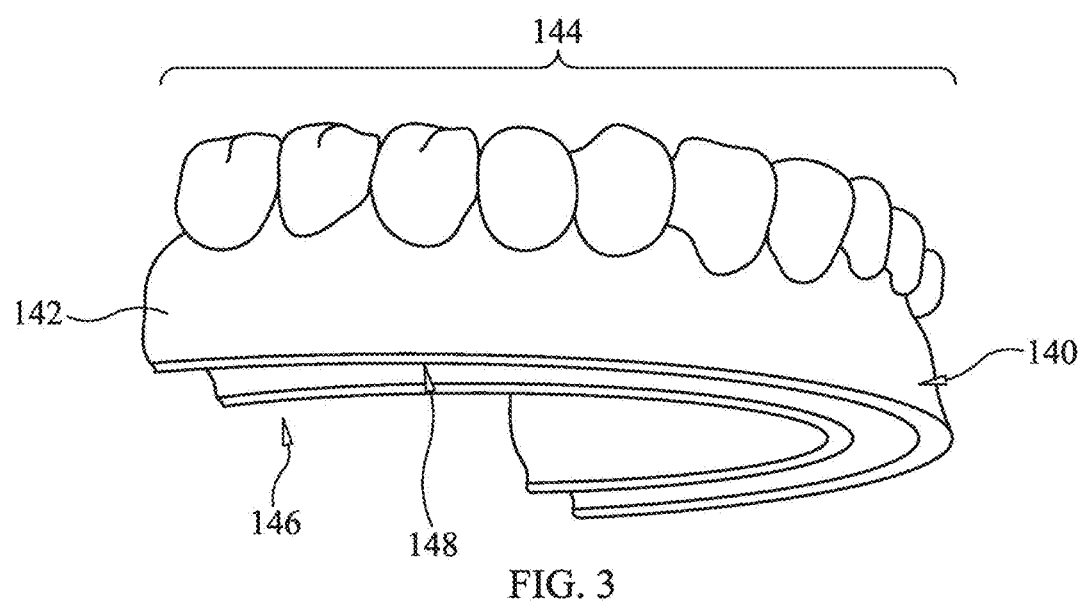
FIG. 3 is substantially a perspective view of one version of the dental prosthesis as used with the present invention.

As substantially shown in FIG. 3, one possible version of the prosthesis 140 could comprise of a prosthesis base 142 providing artificial gingiva or gum, the prosthesis base 142 further supporting one or more artificial teeth 144. The underside 146 of the prosthesis base 142 could further denote a channel 148 that could accept the dental implant surgical guide 120. In other embodiments, not shown, the dental prosthesis could be constructed into halves wherein the dental implant surgical guide in placed between the halves which are then closed together to generally encapsulate the dental implant surgical guide within the dental prosthesis.

Figure 4:
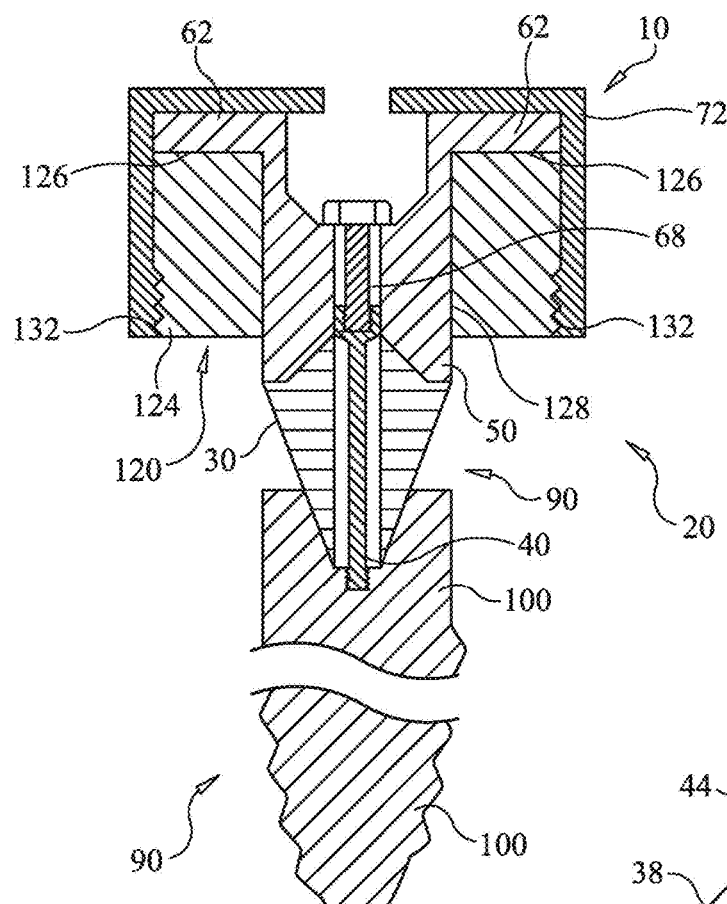
FIG. 4 is substantially a cutaway elevation end view of the assembled system for the present invention.

As shown in FIG. 4, the system 20 could comprise an abutment 30, an implant mount 50 and a cap 72, wherein the abutment 30 may be used to secure the implant mount 50 to the implant 100 to form an implant combination 90, the implant combination 90 being moved through a guide channel 128 to place the implant 100 into the previously prepared implant shaft at the dental surgical site. A fastener-to-fastener connection provided by first and second fasteners 40, 68 may initially hold the implant combination 90 together. The implant mount 50 may have a rim 62 that cannot pass through the guide channel 128 and may be subsequently be drawn against the dental implant surgical guide 120 (as substantially shown in FIG. 11). The cap 72 substantially attaches to a respective guide cylinder 124 to securely seat the rim 62 against the dental implant surgical guide 120. This attachment action may substantially increase the contact of the rim 62 to the dental implant surgical guide 120 thereby bringing the dental implant surgical guide 120 up a desired final position relative to the one or more dental implants 100 placed at the dental surgical site 12.

Figure 5:
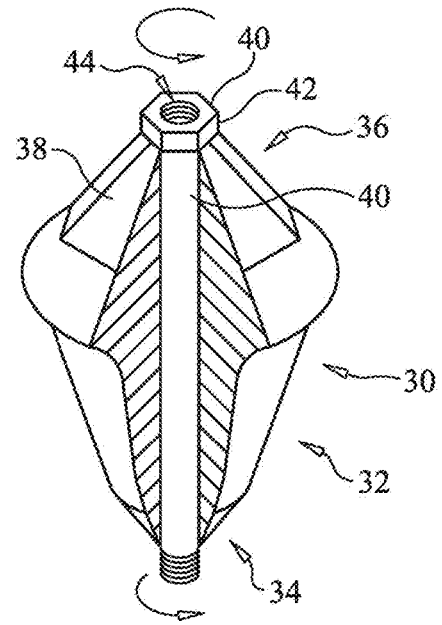
FIG. 5 is substantially a perspective cutaway view of one embodiment of the abutment for the present invention.

As substantially shown in FIG. 5, the abutment 30 could have an abutment body 32 made of suitable material known in the art and the first fastener 40 that may movably penetrate through the abutment body 32. The abutment body 32 may have an overall exterior shape as would be substantially selected by those known in the art that generally promotes a suitable and healthy implant interface with the gum tissue and emergent sulcus. The abutment body 32 could further define a first and second abutment ends 34, 36 through which the first fastener 40 could pass. The first abutment end 34 could be tapered or conical-shaped to be generally reciprocal to the contours of the implant recess 108 to generally provide a taper interference fit (e.g., Morse's taper) between the dental implant 100 and abutment 30 when the first abutment end 34 is placed within the implant recess 108. The second abutment end 36 may have a contour that when received within the implant mount 50 could prevent the abutment 30 from rotating about the implant mount 50. In one possible embodiment, the second abutment end 36 may have a contour formed by a set of inclined flats 38 that may be seen to generally form an overall conical arrangement.

The first fastener 40 could be a threaded fastener and have a first fastener head 42 being large enough so that the first fastener head 42 does not pass through the abutment body 32. The first fastener 40 could be further capable of engaging the implant aperture 112 (e.g., threaded) of an implant recess 108 to initially secure the abutment 40 to the dental implant 100. In one possible embodiment, the first threaded fastener 40 could be generally held captive by the abutment body 32 for safety and efficiency reasons. The first fastener 40 could further be a bolt wherein the bolt's head is shaped with flats for removable engagement by a suitable wrench (not shown). The first fastener head 42 could further feature an open-ended fastener recess 44 to which a second fastener 68 could be attached and generally allowing for the attachment of the implant mount 50 to the abutment 30 (as substantially shown in FIG. 4).

Figure 6:
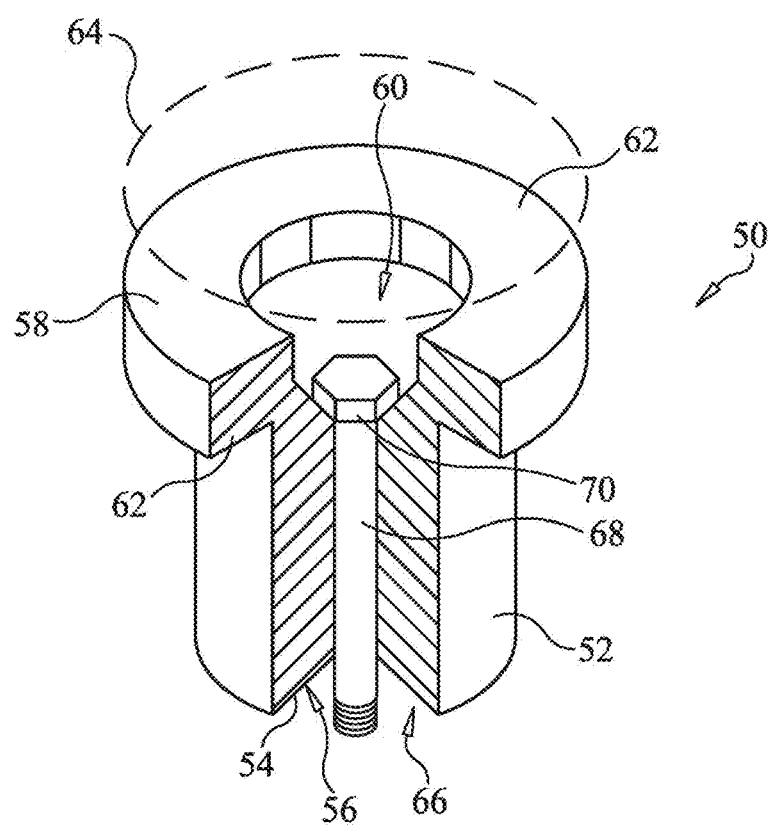
FIG. 6 is substantially a perspective cutaway view of one embodiment of the implant mount for the present invention.

As substantially shown in FIG. 6, the implant mount 50 could comprise a cylindrically-shaped mount body 52 and a second fastener 68 that movable penetrates through the mount body 52. The mount body 52 could be made of suitable materials as known and selected by the art and generally terminating in the first mount end 54 and a second mount end 58. The first mount end 54 could feature an open-ended abutment cavity 56 that has a contour 66 (e.g., inclined flats) that generally matches the form of the second abutment end 36. In this manner, when the second abutment end 36 may be placed within the abutment cavity 56, the second abutment end 36 may engage the abutment cavity 56 in a way that substantially prevents rotation of second abutment end 36 within the abutment cavity 56 (as substantially shown in FIG. 4).

The second mount end 58 could have a mount depression 60 that could accommodate the second fastener head 70 so that second fastener head 70 may not protrude above the second mount end 58 when the second fastener 68 is connected to the first fastener 40. The mount depression 60 could be further suitably fashioned to removably accept a tool 14 that can rotate the assembled or completed implant configuration 90 relative to the dental surgical guide 120, as well as implant shaft 18 (as substantially shown in FIG. 9).

The second mount end 58 may have an outwardly projecting protrusion such as a lip or rim 62 whose overall size is too large to allow the rim 62 fit into or through the guide channel 128 but the remainder of the mount body 52 is sized to pass though the guide channel 128. The rim 62 could have a rim circumference 64 that is generally greater than the circumference of the guide channel 128 but not greater than the circumference of the guide cylinder top 126 to provide sufficient implant mount retention capability.

The second fastener 68 could be also threaded (e.g., be a threaded bolt) and have a second fastener head 70 being large enough so that the second fastener head 70 does not pass through the mount body 52. The second fastener 68 could be further capable of engaging the fastener recess 44 so as to connect (e.g., removably) the second fastener 68 to the first fastener 40. This fastener-to-fastener connection could allow the implant mount 50 to be removably attached to the abutment 30 and further provide for the unification of the implant mount 50, abutment 30 and dental implant 100 when assembled into the implant combination 90 outside the patient's mouth. In this manner, the assembled implant combination 90 can then be inserted into the guide channel 128 and rotated as an single unit to drive and anchor the dental implant 100 into a previously prepared dental surgical site 12 (e.g., implant shaft 18) and to generally bring the rim 62 into contact with the guide cylinder 124 (as substantially shown in FIG. 4).

Figure 7:
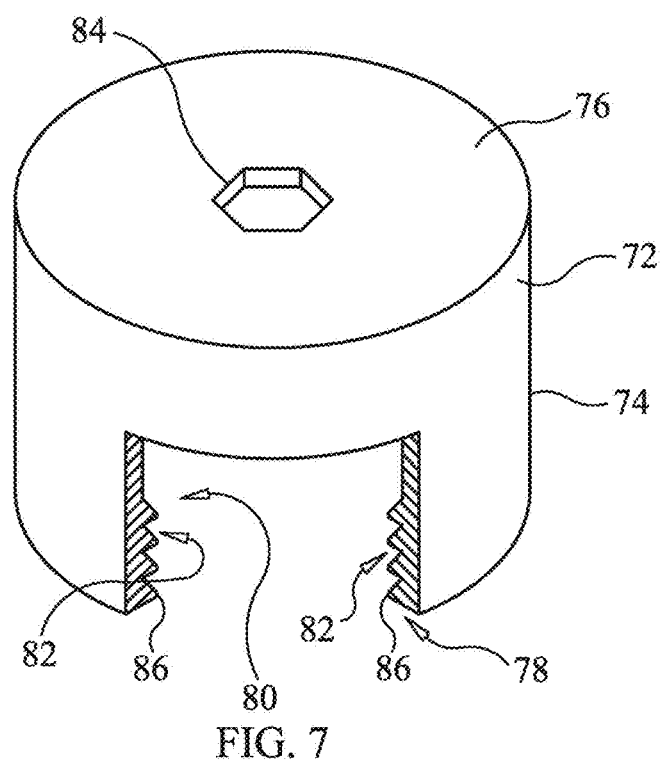
FIG. 7 is substantially a perspective cutaway view of one embodiment of the cap for the present invention.

As substantially shown in FIG. 7, the cap 72 could be a hollow cap cylinder 74 with one enclosed cap end 76 and one open cap end 78. The cap cylinder wall's interior side 80 as proximate to the open cap end 78 could be feature a suitable cap locking interface 82 such as cap threads 86 to generally allow the cap 72 to be removably attached to the guide cylinder 124. As so attached, the cap 72 could generally cover both the second mount end 58 (e.g., rim 62) and the guide cylinder's top 126. The attachment of the cap 72 to the dental implant 100 in such circumstances could also be used to fully bring up the dental implant surgical guide 120 into significant contact with the rim 62. This rim contact could insure that dental implant surgical guide 120 is brought into final and desired telemetry and positioning as relates to the one or more placed dental implants 100. Further, the cap 72 and dental implant surgical guide 120 when so combined may further substantially secure the implant combination 90 to the dental implant surgical guide 120 to generally provide a resistance to those forces pushing the dental implant surgical guide 120 (e.g., as attached to the dental prosthesis 140) toward the one or more located dental implants 100 placed at the dental surgical site 12 (as substantially shown in FIG. 4).

The cap 72 could further have a suitable cap fixture 84 (e.g. such as a hexagon-shaped tool aperture in the center of the enclosed end 76) that can accept a suitable tool (e.g., a wrench-not shown) that can be used to attach (e.g., rotate) the cap 72 onto the dental implant surgical guide 120. In some embodiments, the cap 72 may be removably attached to the dental implant surgical guide 120.

Figure 8:
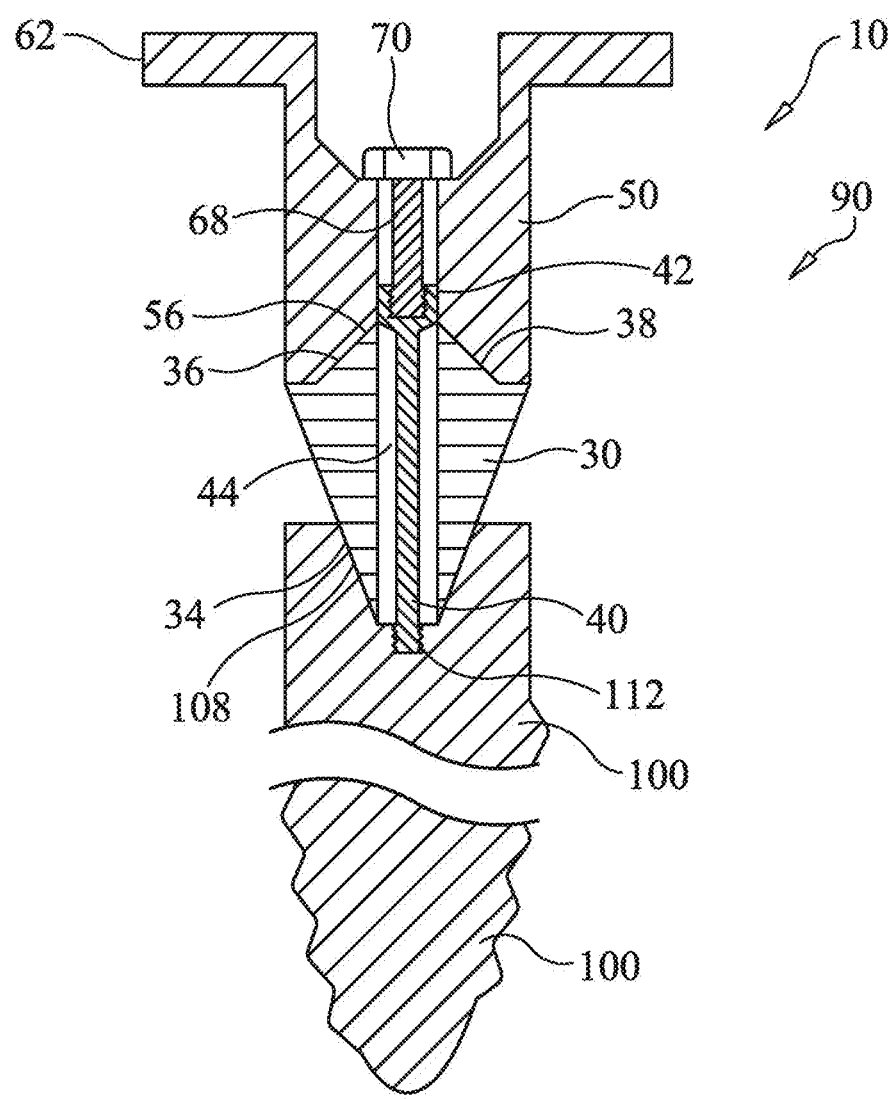
FIG. 8 is substantially a side elevation cutaway view of one embodiment of the implant combination for the present invention.

As substantially shown in FIG. 8, the implant mount 50, the abutment 30 and the implant 100 could be assembled together (e.g., away from the dental implant surgical guide 120, outside of the patient's mouth 12 or both) to form the implant combination 90. The first fastener 40 (generally penetrating the abutment 30) can attach to the implant aperture 112 to bring the abutment 30 and the implant 100 together allowing the first abutment end 34 to mate within the implant recess 108. This tapered mating could bring into a force a taper interference connection (e.g., Morse's taper) between the abutment 30 and the implant 100. The second abutment end 36 can be brought into contact within the abutment cavity 56 of the implant mount 50 so that the flats 38 of the second abutment end 36 and the contour 66 (e.g., inclined flats) of abutment cavity 56 are brought into contact and alignment with one another. The second fastener 68 may further facilitate this contact by substantially engaging the fastener recess 44 in a fastener-to-fastener connection. The second abutment end's inability to rotate within the abutment cavity 56 (e.g., use of reciprocal flats 38) allows a rotation of the implant mount 50 to transmit a torsional force to the combined abutment 30 and implant 100 without placing the second fastener 68 under undue stress (e.g., a shearing force) when driving in the implant 100 into the implant shaft 18. This connection allows the implant mount 50 to be subsequently removed from the placed implant combination 90 (e.g., after being generally anchored at the dental implant site 12) if the dental implant surgical guide 120 needs to be removed from the placed implant combination 90. This same rotation or torsion force as transmitted to the implant combination 90 and hence imparted to the abutment-implant connection should increase the adhesion capability of the taper interference fit.

As substantially shown in FIG. 8, the assembled implant combination 90 can be placed through the guide channel 128 to bring the dental implant 100 into contact with prepared implant shaft 18 as substantially denoted by bone, namely mandible, maxilla. A tool 14 (e.g., a wrench) substantially connects with the mount depression 60 to rotate the assembled implant combination 90 (e.g., relative to both the dental implant surgical guide 120 and the dental surgical site 12) until the dental implant 100 is properly attached to and situated within the dental surgical site 12. If an implant analogue (not shown) is used instead of the implant 100 to form an analogue implant combination (not shown), then tool 14 can be similarly be used to rotate the analogue implant combination to properly attach and situate said implant analogue relative to the model dental surgical site (not shown).

Figure 9:
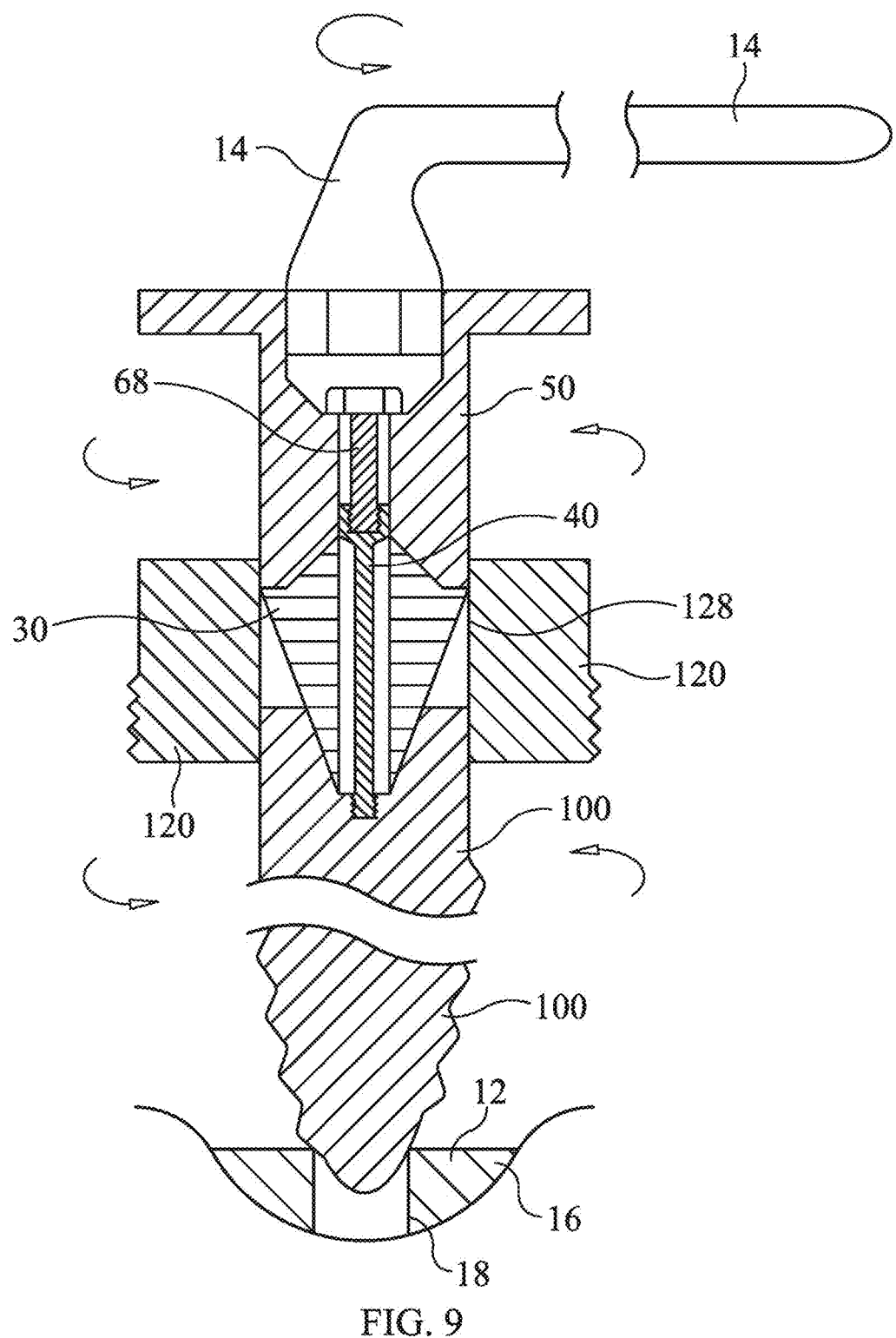
FIG. 9 is substantially an end elevation cutaway view of one embodiment of the implant combination for the present invention as the implant combination is being rotated in the dental implant surgical guide.
Figure 10:
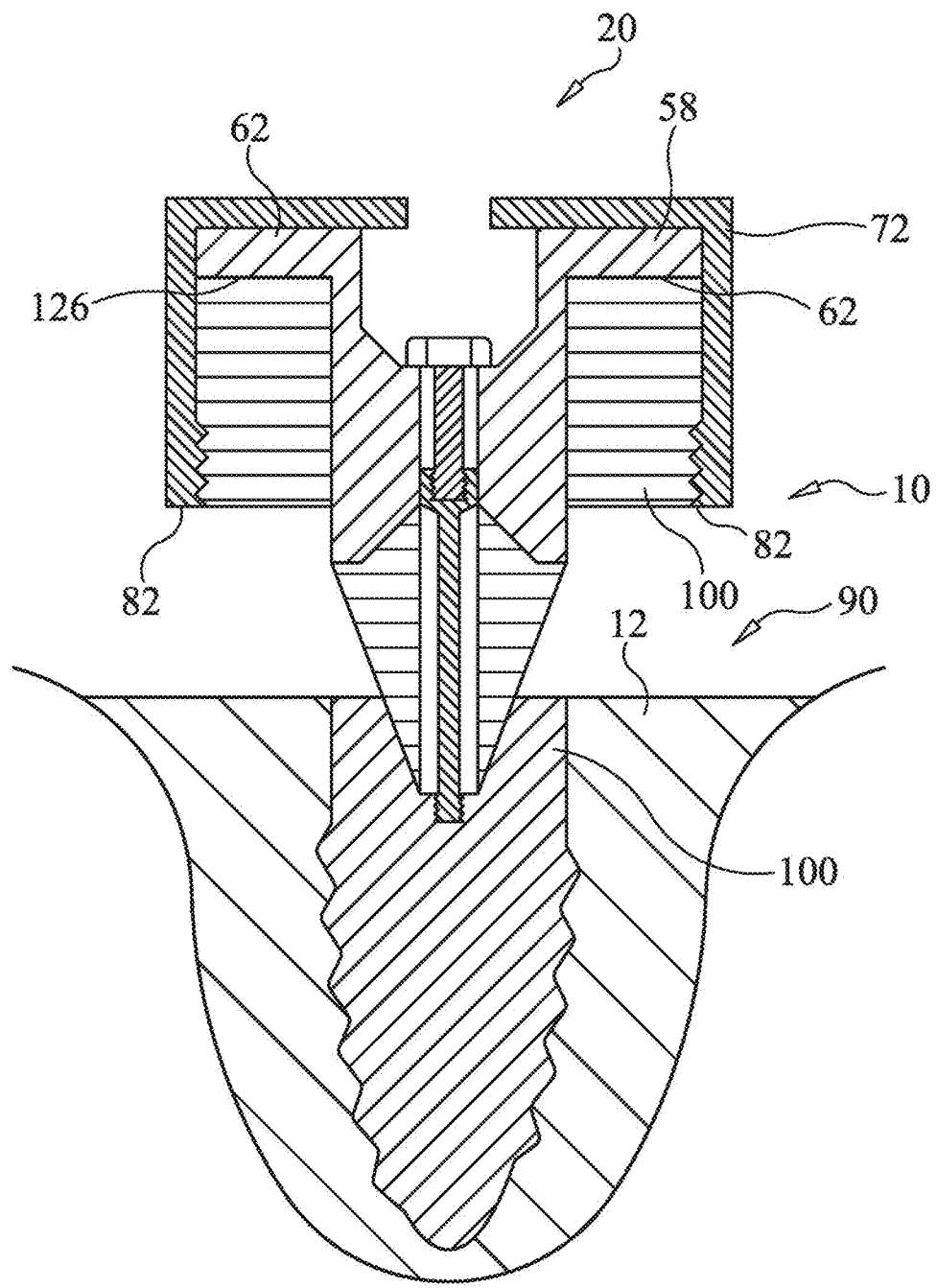
FIG. 10 is substantially a side elevation cutaway view of one embodiment of the implant combination of the present invention with the dental implant surgical guide with cap applied.

As substantially shown in FIG. 9, once the implant combination 90 and alike is suitably placed and secured (e.g., dental surgical site 12, model dental implant site), the cap 72 can be placed over the top 126 of the guide cylinder 124 through which the implant combination 90 (or analogue implant combination-not shown) is generally located. A suitable tool (e.g., wrench-not shown) can engage the cap fixture 84 to substantially move (e.g., rotate) the cap 72 relative to the guide cylinder 124 so that the cap locking interface 82 can engage the locking interface 132 of the guide cylinder 124 to substantially draw the guide cylinder 124 into the cap 72 (e.g., screwing the cap 72 on to the threaded guide cylinder 124.) In this manner, the enclosed cap end 76 can impinge upon the second mount end 58 to securely press upon the rim 62, substantially sandwiching the rim 62 in between the enclosed cap end 76 and the guide cylinder top 126. In this manner, the sandwiched rim 62 could fully anchor the dental implant surgical guide 120 to the dental surgical site 12. This attachment combination may further resist those forces, which may attempt to move the dental implant surgical guide 120 (e.g., the attached prosthesis) away from or to the one or more implants 100 to which the dental implant surgical guide 120 is secured.

The cap attachment could be one of the last steps undertaken prior to the attachment of the prosthesis 140 to the dental implant surgical guide 120. In that manner, the attachment of caps 72 to the respective implant combinations 90 as place through the guide channels 128 of the dental implant surgical guide 120 could be accomplished using an alternating sequence, such as tightening first the caps 72 located proximate to the back of the mouth 16 and moving towards those caps 72 located proximate to the front of the mouth 16.

Figure 11:
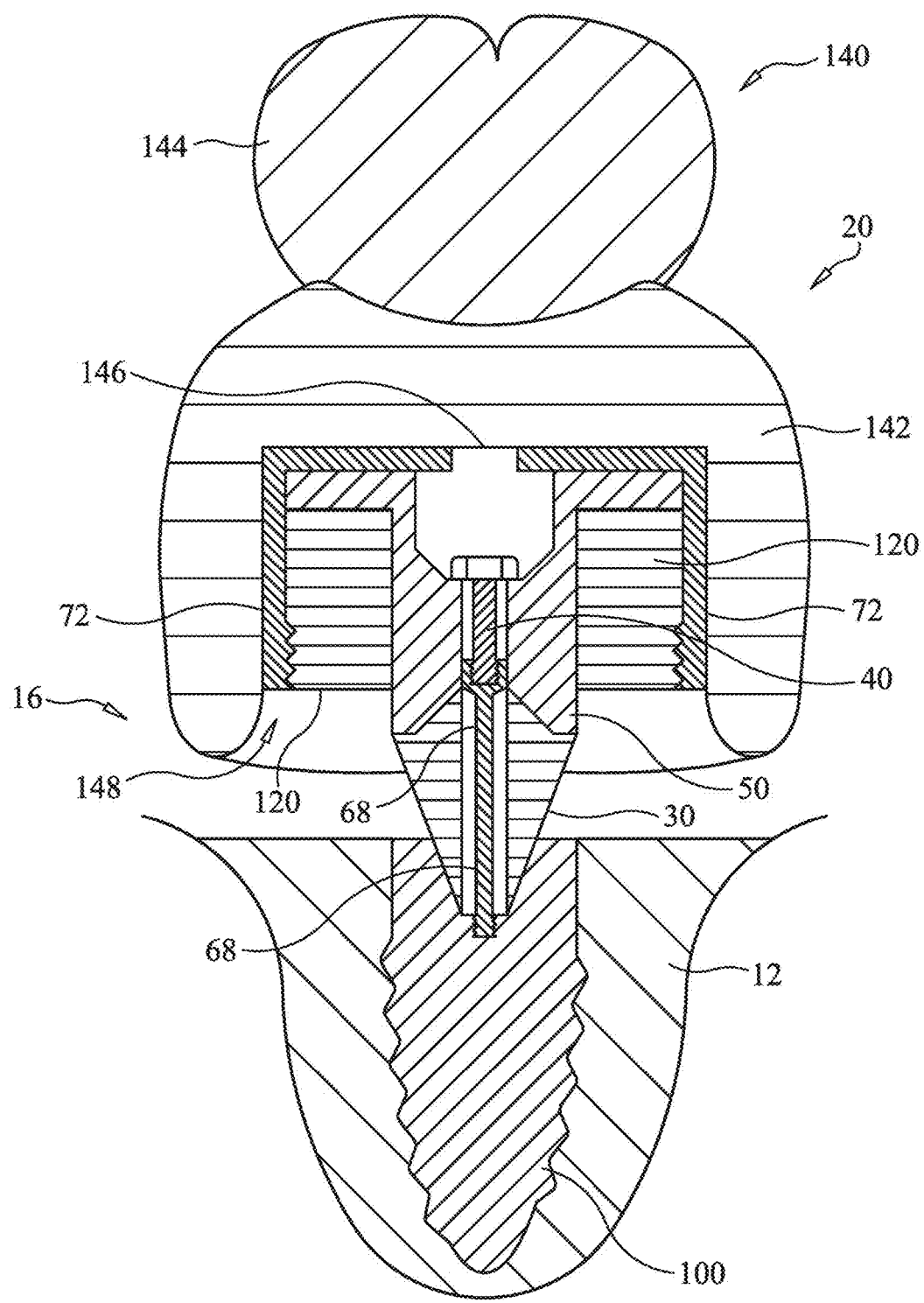
FIG. 11 is substantially a side elevation cutaway view of one embodiment of the implant combination for the present invention anchoring the dental implant surgical guide with a prosthesis attached.

As substantially shown in FIG. 11, once the caps 72 have been appropriately secured to the dental implant surgical guide 120, the prosthesis 140 can be secured to the dental implant surgical guide 120. In the embodiment using an enveloping dental prosthesis (not shown), the bottom half of the prosthesis could be attached to the dental implant surgical guide prior to the attachment by the system. The bottom half and dental implant surgical guide as combined could then be attached to the mouth using the system. Once so secured, the caps could be attached to the dental implant surgical guide and the top half of the prosthesis placed over the bottom half to substantially encapsulate the dental implant surgical guide within the enveloping dental prosthesis.

Figure 12:
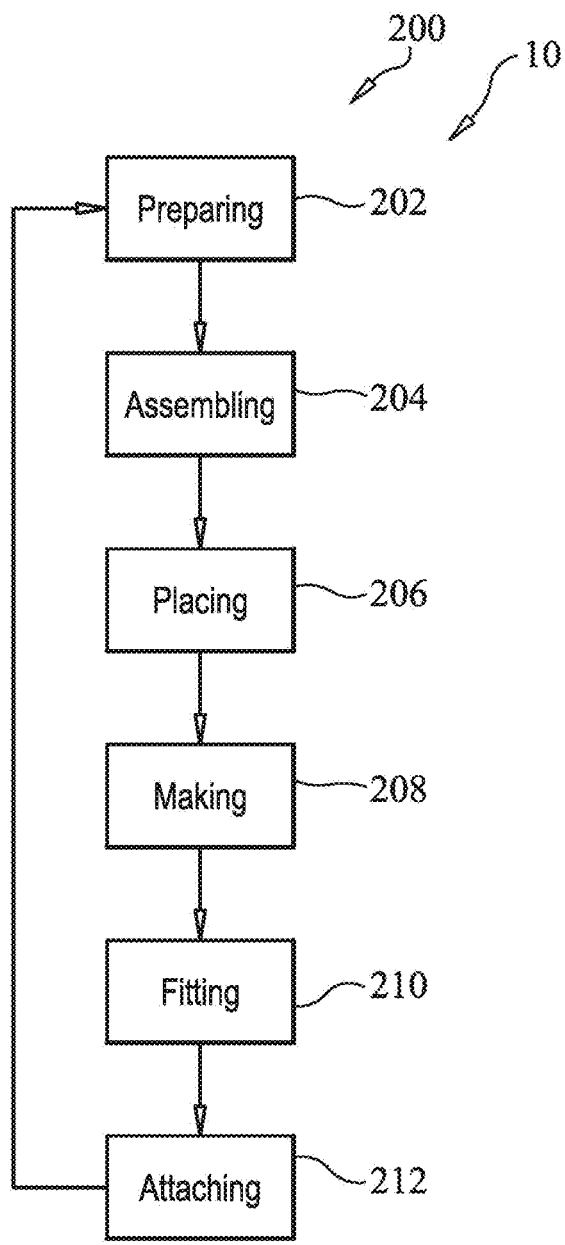
FIG. 12 is substantially a flowchart schematic showing one possible embodiment of a process or a method for operating the present invention.

As substantially shown in FIG. 12, the process or method 200 of using the invention 10 could start with step 202, preparing the dental surgical site. In preparing the dental surgical site, the dental implant surgical guide could be suitably be brought proximate (e.g., attached by suitable method and means) to the dental surgical site. Dental implants (e.g., implant drills, implant reamers, and the like) could pass into respective guide channels to be directed to create the implant shafts that could receive dental implants. When this step is substantially completed, the process 200 could proceed to step 204, the assembling of the implant combination. For the encapsulating prosthesis, the bottom half of the prosthesis could be attached to the dental implant surgical guide.

In step 204, the assembling of the implant combination, the abutment can be first attached to the implant with the first abutment end being placed into the implant recess for a generally conical fit that can result in a taper interference fit or Morse's taper connection. The first fastener movably located through the abutment can then attach to the implant aperture at the tip of the conical fit to further hold the abutment and implant together. The implant mount can be connected to the abutment by placing the second abutment end within the abutment cavity of the implant mount so that the flats of the abutment cavity may be aligned with the flats of the second abutment end. The second fastener, movably located in the implant mount, may removably attach to the head of the first fastener to generally hold the implant mount in place upon the second abutment end and to generally complete the assembly of the implant combination. Depending on the number of dental implants that are needed, this step can be repeated several times to complete several implant combinations. Once this step is substantially completed, process 200 could proceed to step 206, placing the dental implant.

In step 206, placing the dental implant, the implant combination could be guided through the guide cylinder top to pass at least a portion of the implant combination through a respective guide channel (and through the bottom prosthesis half). The tip of the implant could initially engage the respective previously prepared implant shaft at the dental surgical site. If an implant analogue is used instead of the dental implant in the assembly of the implant combination, the implant analogue could be directed to an implant analogue shaft at a dental surgical site model. A suitable tool could be attached the second mount end (e.g., a wrench attached to the mount fixture) and the operator such as a dental health care professional can rotate the entire implant combination within the guide cylinder to drive the implant (e.g., or implant analogue) into the implant shaft. Once the implant and hence implant combination is firmly and properly seated within the dental surgical site, the step can be repeated for each additional implant combination that needs to be attached to the dental surgical site (or the dental surgical site model). Generally during this action, the second mount end is substantially brought into closer proximity to the respective cylinder, namely the rim may make contact with guided cylinder top. As this step is substantially completed, the process 200 may proceed to step 208, making adjustments.

In step 208, making adjustments, this is an optional step wherein the implant mount may need to be released from a placed implant combination to allow for removal of the dental implant surgical guide (prosthesis bottom half) from the implant combination. In such a situation, the second fastener may be disconnected from the first fastener so that the implant mount may be removed from the abutment. Depending on the number of implant combinations being located at that time, their respective implant mounts may need to be removed to allow for the full detachment of the dental implant surgical guide from the dental surgical site (or the dental surgical site model).

Once the adjustment, correction, fitting, or the alike has been be made, the dental implant surgical guide could be replaced over the abutments and the implant mounts could be suitably reattached to their respective abutments. This step can be repeated as needed to make the many adjustments, corrections, fittings, or the alike as needed. Once this step is substantially completed, the process 200 could proceed to step 210, fitting the cap.

In step 210, fitting the cap, the cap could be applied to a respective guide cylinder. A suitable tool (e.g., wrench) could be applied to mount fixture on the cap's enclosed end. The cap open end could be directed to and engage the top of the respective cylinder (e.g., the cylinder substantially holding the placed implant combination) so that the cap locking interface (e.g., cap threads) can engage the guide cylinder's locking interface (guide threads). Once the cap has fully engaged the guide cylinder, the tool can be removed. For multiple cap/guide cylinder applications, the caps can be applied and tighten in sequenced order that substantially eliminates possible warped placement of the dental implant surgical guide to the implants and to generally ensured dental implant surgical guide achieves the desired telemetry and position relative to the implants (and patient's mouth).

It should be noted that if needed the caps could be removed from guide cylinders, the implant mounts from the abutments, to release the dental implant surgical guide from the implants (or implant analogues).

As this step is substantially completed, the process 200 could proceed to step 212 attaching the prosthesis. In one version of the prosthesis, the dental implant surgical guide could be attached to the base channel. For the encapsulating or enveloping prosthesis, the prosthesis top half could be attached to the combined dental implant surgical guide and prosthesis bottom half to secure and envelope the dental implant surgical guide within the prosthesis. At the substantial completion of this step, the process 200 could proceed back to step 202 as needed.

CONCLUSION

Although the description above contains many specifications, these should not be construed as limiting the scope of the invention but as merely providing illustrations of some of the presently preferred embodiments of this invention. Thus, the scope of the invention should be determined by the appended claims and their legal equivalents rather than by the examples given.

As substantially shown in the drawings and generally described in the description, the invention could be a system for attachment of a dental implant surgical guide to one or more implants that allow the dental implant surgical guide to support a prosthesis and secure the prosthesis to the patient's mouth. The system could provide an implant combination that can be used to rotate an implant into place in a dental surgical site. In doing so the implant combination can bring a rim from the implant combination into contact with the guide cylinder top of the dental implant surgical guide. A cap attaching to the rim and dental implant surgical guide can then lock the dental implant surgical guide in place with one or more implant combinations to appropriately attach the dental implant surgical guide to the patient's mouth, allowing the dental implant surgical guide to anchor and support a dental prosthesis.

What is claimed is:

1. A method for attaching a dental implant surgical guide and a dental implant to a dental surgical site, the method comprising:
    assembling an implant combination comprising:
        a dental implant comprising a first implant end operable to attach to the dental surgical site and a second implant end operable to attach to an abutment,
        an implant mount comprising an implant mount body with a first mount end operable to connect to a portion of the abutment and a second mount end comprising a rim that cannot pass through the dental implant surgical guide, and
        an abutment comprising a first end and a second end,
    wherein assembling the implant combination comprises:
        attaching the first implant end to the first end of the abutment, and
        connecting the first mount end of the implant mount body to the second end of the abutment;
    positioning the dental implant surgical guide comprising a double open-ended guide cylinder at the dental surgical site;
    rotating the implant combination through the double open-ended guide channel such that the first implant end is secured to the dental surgical site; and
    attaching a cap comprising a hollow cylinder to the double open-ended guide channel such that the rim of the implant mount body is sandwiched between the dental surgical guide and the cap.

2. The method of claim 1, wherein the cap fits over the rim to attach to a top portion of the double open-ended guide channel.

3. The method of claim 1,
    wherein the dental implant surgical guide further comprises a first double open-ended guide cylinder connected to a second double open-ended guide cylinder by a support bar, and
    wherein the method further comprises mounting a prosthesis to the dental implant surgical guide.

4. The method of claim 3,
    wherein the prosthesis comprises a prosthesis base supporting one or more artificial teeth, and
    wherein the prosthesis base comprises a base channel configured to accept the dental implant surgical guide.

5. The method of claim 3, wherein the prosthesis is configured as a first half and a second half, and the method further comprises encapsulating the dental implant surgical guide within the prosthesis by connecting the first half to the second half.

6. The method of claim 1 further comprising passing a tool through the double open-ended guide channel to generate an implant shaft,
    wherein the tool comprises at least one of an implant drill, an implant reamer, and the dental implant.

7. The method of claim 1,
    wherein the implant mount is configured to receive at least a portion of a first fastener,
    wherein the abutment further comprises an abutment body configured to receive at least a portion of a second fastener,
    wherein the first fastener is configured to attach to the second fastener,
    wherein assembling the implant combination further comprises:
        inserting at least a portion of the first fastener through the implant mount, inserting at least a portion of the second fastener through the abutment, and attaching the first fastener to the second fastener.

8. The method of claim 7,
wherein the second implant end of the dental implant further comprises an implant recess configured to receive a portion of the abutment and an implant aperture configured to receive the first fastener, and
wherein assembling the implant combination further comprises inserting the first fastener into the implant aperture to secure the abutment to the dental implant.

9. The method of claim 7, wherein the first fastener comprises a first fastener head configured to be unable to pass through the abutment body.

10. The method of claim 7, wherein the first fastener comprises a first fastener head configured to engage with a wrench, and wherein inserting at least a portion of the first fastener through the implant mount comprises engaging the first fastener using a wrench to secure the abutment to the dental implant.

11. A dental prosthesis apparatus comprising:
an abutment comprising a first end and a second end;
a dental implant comprising a first implant end operable to attach to a dental surgical site and a second implant end operable to attach to the abutment;
a dental implant surgical guide comprising a first double open-ended guide cylinder connected to a second double open-ended guide cylinder by a support bar;
an implant mount comprising an implant mount body with a first mount end connected to a portion of the abutment and a second mount end comprising a rim that cannot pass through the dental implant surgical guide; and
a cap comprising a hollow cylinder with an enclosed cap end and an open cap end, the cap being operable to engage the dental implant surgical guide and sandwich the rim between the cap and the dental implant surgical guide.

12. The dental prosthesis apparatus of claim 11, further comprising a prosthesis mounted to the dental implant surgical guide.

13. The dental prosthesis apparatus of claim 11, wherein the support bar has a trapezoidal cross-shape.

14. The dental prosthesis apparatus of claim 12, wherein the prosthesis comprises a prosthesis base supporting one or more artificial teeth, and wherein the prosthesis base comprises a base channel operable to accept the dental implant surgical guide.

15. The dental prosthesis apparatus of claim 11,
wherein the cap is threaded on an inside of the hollow cylinder proximate to the open cap end, and
wherein an exterior surface of at least one of the first double open-ended guide cylinder and the second double open-ended guide cylinder is threaded to receive the cap.

16. The dental prosthesis apparatus of claim 11, wherein the implant mount has a recess and the abutment is configured to prevent the abutment from rotating within the recess.

17. The dental prosthesis apparatus of claim 16,
wherein the recess comprises a set of inclined flats,
and wherein a portion of the abutment received within the recess is contoured to match the set of inclined flats.

18. The dental prosthesis apparatus of claim 11 further comprising a first fastener, the first fastener penetrating the abutment and attaching the abutment to the dental implant.

19. The dental prosthesis apparatus of claim 18 further comprising a second fastener, the second fastener penetrating the implant mount and removably attaching the implant mount to the abutment.

20. The dental prosthesis apparatus of claim 19 wherein the second fastener is removably attached to the first fastener.

* * * * *